(12) United States Patent
Leyer et al.

(10) Patent No.: US 8,291,749 B2
(45) Date of Patent: Oct. 23, 2012

(54) IMMERSION PROBE FOR WATER ANALYSIS, COMPRISING AN ELECTRODE FOR DETECTING AN ANALYTE IN WATER

(75) Inventors: Axel Leyer, Moenchengladbach (DE); Lothar Heidemanns, Korschenbroich (DE); Andreas Jonak, Meerbusch (DE); Markus Hahn, Kempen (DE); Michael Kussmann, Duesseldorf (DE); Heinz Rudde, Hueckelhoven (DE); Claudia Rieger, Duesseldorf (DE)

(73) Assignee: Hach Lange GmbH, Berlin (DE)

( * ) Notice: Subject to any disclaimer, the term of this patent is extended or adjusted under 35 U.S.C. 154(b) by 241 days.

(21) Appl. No.: 12/778,350

(22) Filed: May 12, 2010

(65) Prior Publication Data

US 2010/0288023 A1 Nov. 18, 2010

(30) Foreign Application Priority Data

May 14, 2009 (EP) ..................................... 09160273

(51) Int. Cl.
*G01N 11/00* (2006.01)
(52) U.S. Cl. ..................................... 73/53.01; 73/866.5
(58) Field of Classification Search ...... 73/53.01–53.07, 73/1.06, 1.07, 45.5, 866.5
See application file for complete search history.

(56) References Cited

U.S. PATENT DOCUMENTS

| | | | |
|---|---|---|---|
| 6,360,875 B1 * | 3/2002 | Altemus et al. | 198/499 |
| 6,582,263 B1 * | 6/2003 | Jaeger et al. | 440/89 C |
| 7,110,887 B2 * | 9/2006 | Harima et al. | 702/23 |
| 7,300,001 B2 * | 11/2007 | Kuo | 239/333 |
| 7,367,222 B2 * | 5/2008 | Kahn et al. | 73/53.01 |
| 2005/0005717 A1 * | 1/2005 | Pensis et al. | 73/866.5 |
| 2007/0197856 A1 * | 8/2007 | Gellman et al. | 600/16 |
| 2008/0067065 A1 * | 3/2008 | Feng | 204/415 |

OTHER PUBLICATIONS

"Dissolved Oxygen Measurement System with Air Blast Cleaner", Product Instruction Manual 51-DO-03/04/rev.C, Rosemount Analytical, Oct. 2004, Pertinent pp. 1-11, 41, 50-53.*
"Dissolved Oxygen Measurement System with Air Blast Cleaner", Product Instruction Manual 51-DO-03/04/rev.C, Rosemount Analytical, Oct. 2004, Pertinant pp. 1-11, 41, 50-53.*

* cited by examiner

*Primary Examiner* — Hezron E Williams
*Assistant Examiner* — David Z Huang
(74) *Attorney, Agent, or Firm* — Norman B. Thot

(57) ABSTRACT

An immersion probe for water analysis includes at least one electrode configured to detect an analyte in water, a probe head with a probe head end side on which the at least one electrode is disposed, and a separate protective cap attached to the probe head so as to be removable in a distal direction. The separate protective cap includes a protective cap end side with an electrode opening and an air discharge nozzle. The air discharge nozzle is configured so as to cause air exiting the air discharge nozzle to sweep over the at least one electrode.

8 Claims, 3 Drawing Sheets

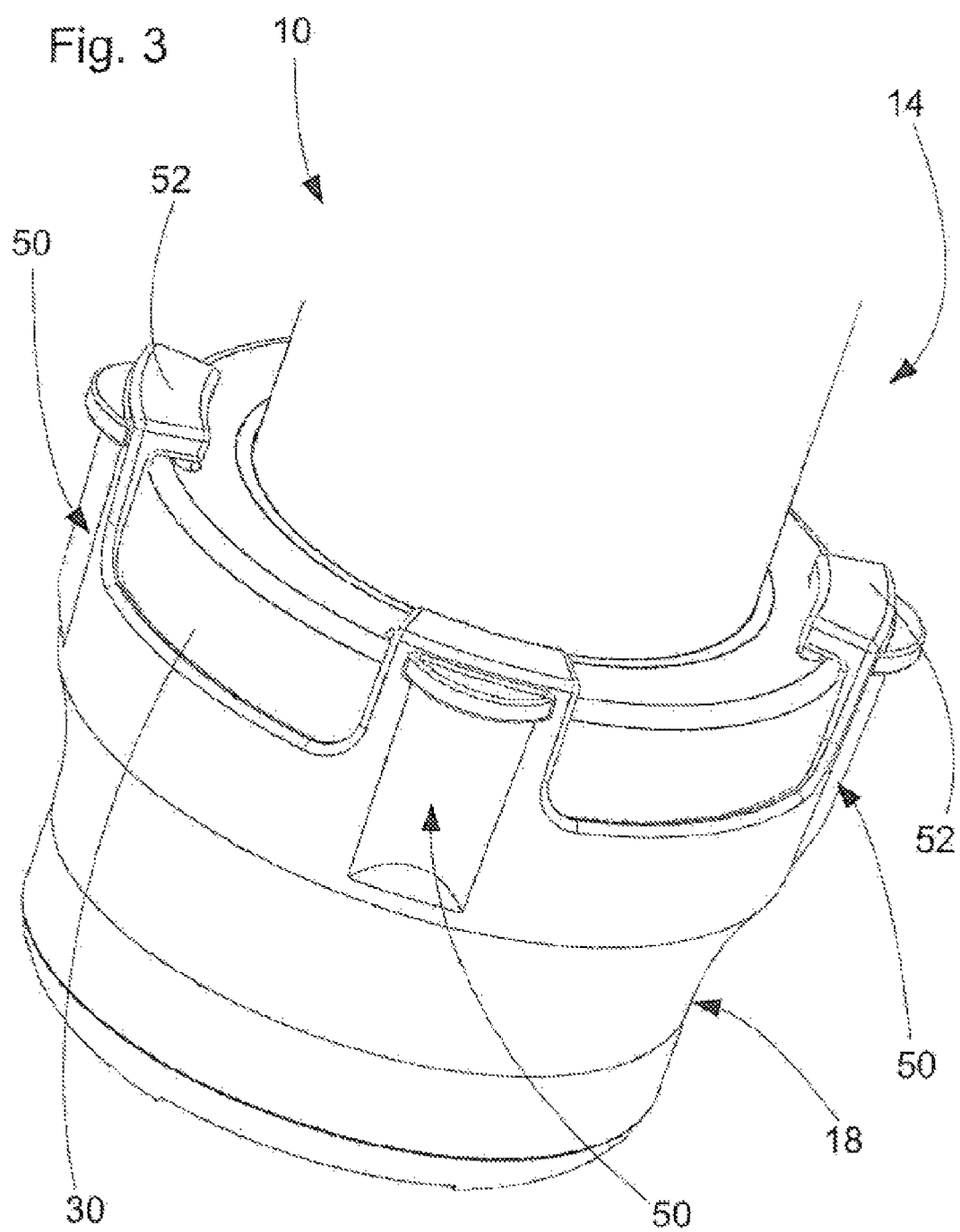

IMMERSION PROBE FOR WATER ANALYSIS, COMPRISING AN ELECTRODE FOR DETECTING AN ANALYTE IN WATER

CROSS REFERENCE TO PRIOR APPLICATIONS

Priority is claimed to European Patent Application No. EP 09160273.0-2204, filed May 14, 2009. The entire disclosure of said application is incorporated by reference herein.

FIELD

The present invention relates to an immersion probe for water analysis which includes an electrode for detecting an analyte in water.

BACKGROUND

Water-analysis immersion probes are used for process analysis in wastewater purification, quality control of drinking water etc. in order to perform a quasi-continuous determination of one or a plurality of specific analytes in water. For this purpose, the immersion probe comprises, on its end side, one or a plurality of electrodes which are prone to fouling and obstruction. Such fouling and obstruction can be precluded by scavenging the end side of the immersion probe with air. State-of-the-art immersion probes adapted to be scavenged by air have a relatively complex design, so that the disassembly and assembly of the immersion probe for maintenance and repair purposes is bothersome.

SUMMARY

An aspect of the present invention is to provide an immersion probe adapted to be scavenged by air with simplified disassembly and assembly processes.

In an embodiment, the present invention provides for an immersion probe for water analysis which includes at least one electrode configured to detect an analyte in water, a probe head with a probe head end side on which the at least one electrode is disposed, and a separate protective cap attached to the probe head so as to be removable in a distal direction. The separate protective cap includes a protective cap end side with an electrode opening and an air discharge nozzle. The air discharge nozzle is configured so as to cause air exiting the air discharge nozzle to sweep over the at least one electrode.

BRIEF DESCRIPTION OF THE DRAWINGS

The present invention is described in greater detail below on the basis of embodiments and of the drawings in which:

FIG. 3 is a perspective rear view of the probe head shown in FIG. 1.

DETAILED DESCRIPTION

Figure 1:
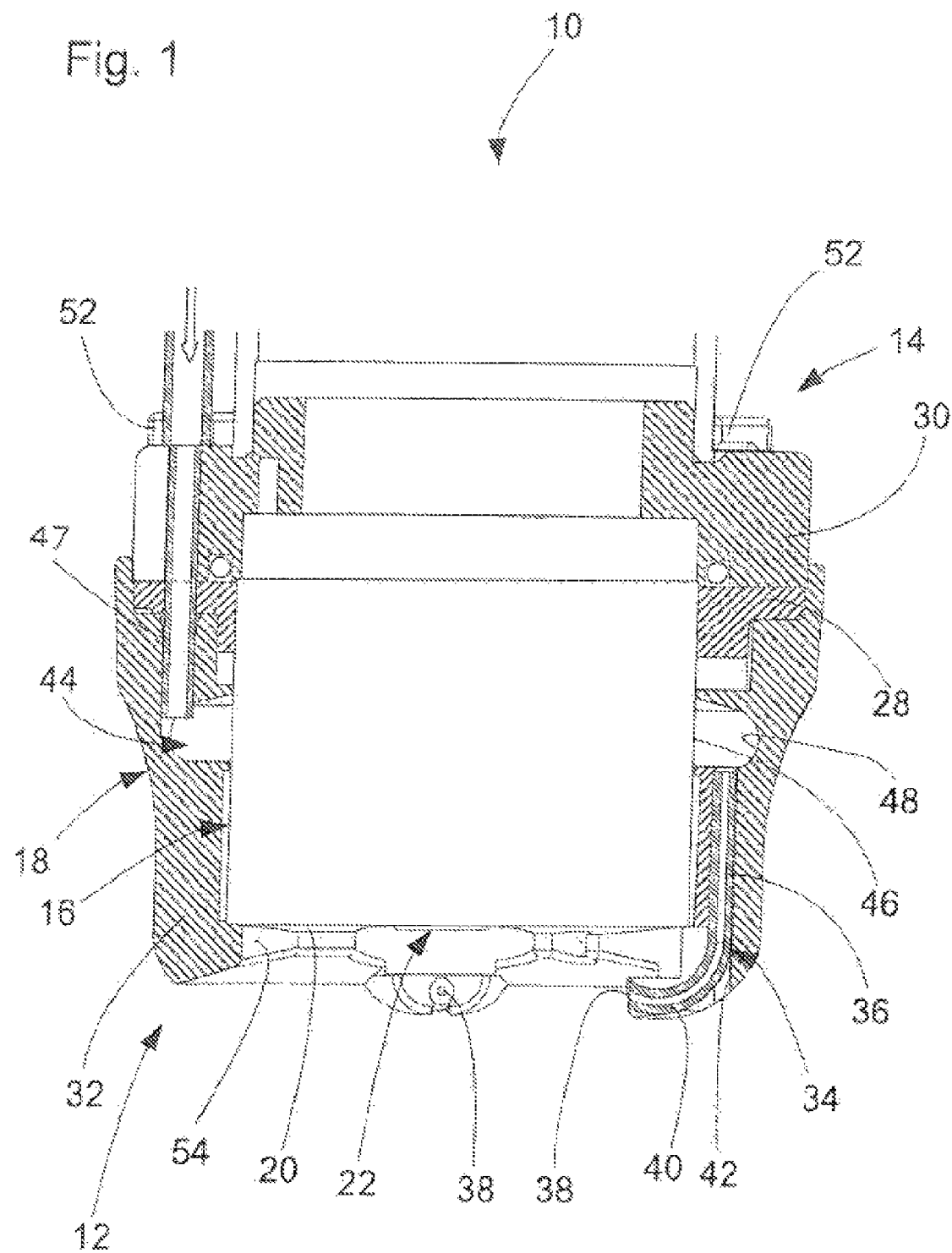
FIG. 1 is a longitudinal sectional view of a probe head of a water-analysis immersion probe.

The water-analysis immersion probe of the present invention comprises an electrode arranged on the end side of its probe head. Attached to its probe head is a separate protective cap which can be removed in the distal direction and on its end side comprises an electrode opening and an air discharge nozzle. Said air discharge nozzle is oriented in such a manner that the air exiting from the nozzle will sweep over the electrode. The air discharge nozzle is directed, for example, towards the electrode.

In the most general sense, the protective cap also has a mechanical protective function for the probe head and is arranged to surround the probe head laterally and partially on the end side, too. On the end side, the protective cap is formed with an electrode opening for one or a plurality of electrodes which are in immediate contact with the water and are not covered by the protective cap. However, it can be provided that the electrodes are arranged in recessed positions within the electrode opening. By the protective cap, the probe head and particularly the electrodes are protected from objects floating about in the water. The protective cap can be withdrawn from the probe head in the distal direction, i.e. downwards in the situation when the immersion probe has been lowered into the water. When withdrawing the protective cap, the air discharge nozzle will remain on the cap. The air discharge nozzle is axially coupled to the scavenging air source via a simple coupling element. The protective cap can, for example, be detachably fixed to the probe head or the probe body with the aid of fastening means allowing for convenient detachment or closure.

In an embodiment of the present invention, the protective cap includes a circular annular air channel and an axial air channel, the latter provided to conduct scavenging air from said circular channel into the air discharge nozzle. The annular channel primarily has the function of distributing the scavenging air along the entire circumference of the protective cap in order to supply scavenging air to a plurality of axial air channels which are distributed along the circumference. On the other hand, the annular channel can also comprise an air inlet opening arranged to lead into a corresponding air supply conduit. The total volume of the annular channel and of the axial air channels should be as small as possible so that the water (which, when the immersion probe has been immersed into the water, has a pressure above the atmospheric pressure) will intrude merely to the slightest possible extent into the axial air channels. The small gas volume is achieved by giving the annular channel the smallest possible size and by realizing the axial transport of the scavenging air via very small axial channels, e.g. via capillaries.

In an embodiment of the present invention, the annular channel is formed proximally by an outer wall of the probe head and distally by the protective cap. The protective cap thus itself comprises a proximally open annular channel whose proximal opening is closed only by the outer wall of the probe head. By the omission of an in-itself-closed annular channel in the protective cap, the protective cap can be produced in a relatively simple manner.

The axial air channel can, for example, be formed by a separate air conducting tube which is axially inserted into the body of the protective cap. For this purpose, the protective-cap body comprises merely an axial bore extending up to the annular channel and axially accommodating said air conducting tube. On its distal ends, the air conducting tube can comprise a bend of 80° to 120° through which the air will finally be discharged substantially in radial directions. The air conducting tube can, for example, be made of stainless steel.

According to an embodiment of the present invention, the probe head is formed by a sensor cartridge which can be separately exchanged. The sensor cartridge can include the electrodes which normally are subjected to wear and should be exchanged at regular intervals. The sensor cartridge can also comprise an electrolyte, disposed in a tank, which will also be exhausted after a certain period of time. By exchanging the sensor cartridge, all electrodes and all other consumable materials can be exchanged in just one working step. Prior to exchanging the sensor cartridge, it is merely required to withdraw the protective cap from the sensor cartridge, and after mounting the new sensor cartridge, all that is needed is simply to reinstall the protective cap on the sensor cartridge.

According to an embodiment of the present invention, the protective cap can be provided with at least two locking tabs for locking attachment on the body of the immersion probe. Such locking tabs will normally be fully sufficient for attaching the probe head to the immersion probe body. For maintenance or repair work to be performed on the immersion probe, the locking tabs can also be opened in a very convenient manner by hand so as to allow the protective cap to be withdrawn. In this manner, removal or fixation of the protective cap can be performed without the need for any tool.

The electrode can comprise, for example, a membrane such as an ion-selective membrane, on its end side. When arranged in water, for example, in waste water, such membranes are subjected to wear and thus, for keeping them free of agglomeration of fouling, have to be continuously scavenged by use of scavenging air.

According to an embodiment of the present invention, the protective cap is formed by a one-pieced protective-cap body which can, for example, be made of rubber-elastic plastic. Such a rubber-elastic plastic body can provide a particularly effective mechanical protection of the probe head from colliding objects. The elasticity of the protective-cap body also makes it possible to realize a simple closure mechanism, for example, in the form of two or more locking tabs.

Figure 2:
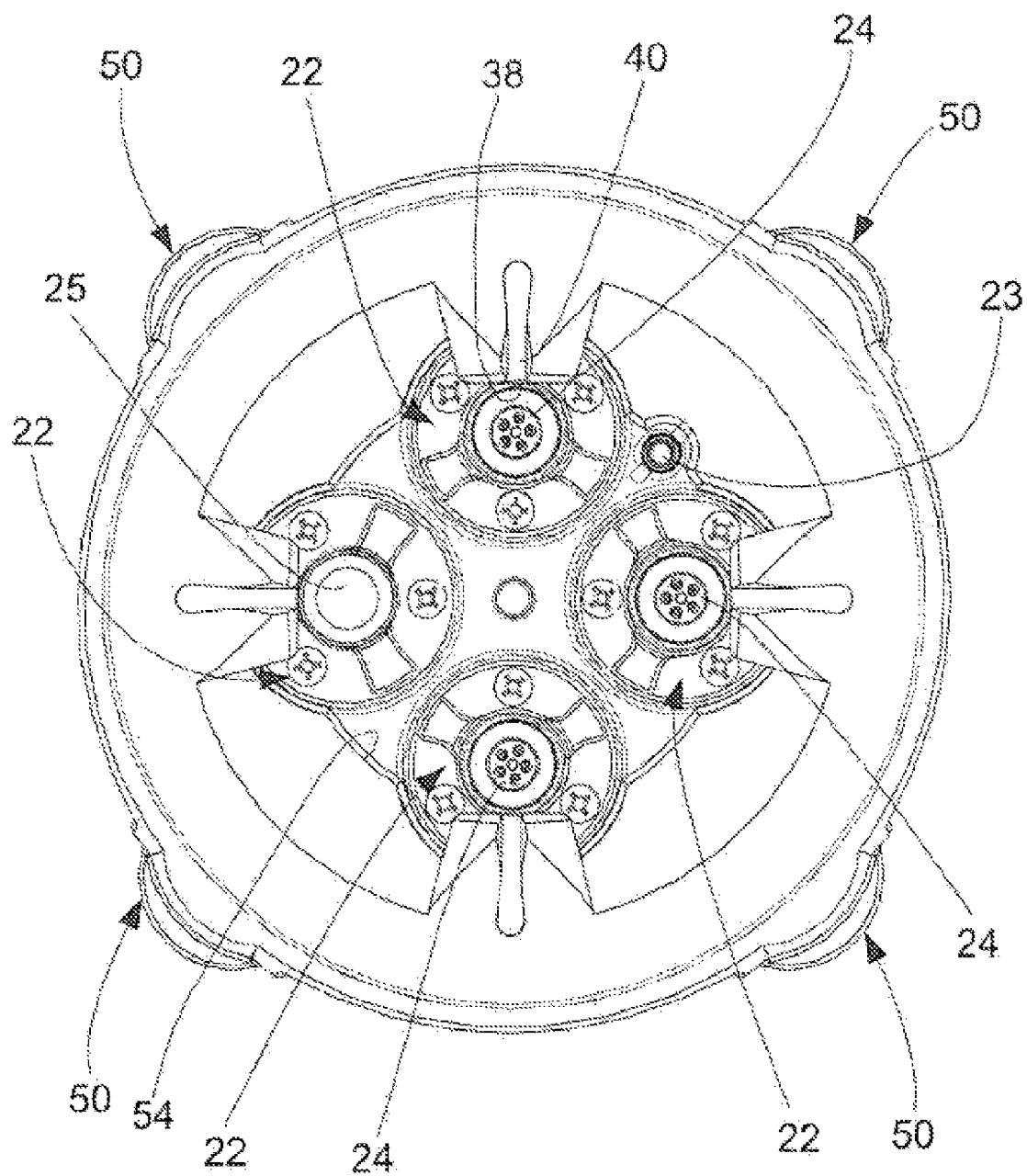
FIG. 2 is a plan view onto the end side of the probe head shown in FIG. 1.

Illustrated in FIGS. 1 to 3 is a water-analysis immersion probe 10 including a probe head 12. Said immersion probe 10 serves for quantitative determination of three different analytes in waste water. Immersion probe 10 substantially includes an immersion-probe body 14, a sensor cartridge 16 fastened thereto, and a protective cap 18 enclosing the sensor cartridge 16.

Sensor cartridge 16 is provided, on its end side 20, with four electrodes 22 and with a so-called salt bridge 23. An element of the electrodes 22 and of the salt bridge 23 includes their respective membranes 24, 25 or metrologically sensitive surfaces which are vulnerable to agglomeration of fouling and to obstruction. Internally of sensor cartridge 16, a tank for an electrolyte is arranged. Sensor cartridge 16 is formed with a surrounding flange 28 which is fastened to a corresponding surrounding flange 30 of immersion-probe body 14 with the aid of suitable fastening means, for example, by screws. Sensor cartridge 16 can be detached from immersion-probe body 14 by disengaging said screws, and is provided with electric plugs releasably engaged with corresponding electric plugs of immersion-probe body 14. Sensor cartridge 16 is designed as an exchangeable unit.

Protective cap 18 includes a one-pieced protective-cap body 32 of rubber-elastic plastic, the body being distally provided with an electrode opening 54 on the end side. Cap 18 also includes four air-conducting tubes 34 of stainless steel forming respectively one axial air channel 36 and including an air discharge nozzle 38. Distally, the air-conducting tubes 34 include respectively a bend 40 of about 110° whereby the air discharge nozzles 38 are given a radial and slightly proximal orientation. Each of the four air discharge nozzles 38 is associated to respectively one electrode 22 and to the salt bridge 23, respectively, and is precisely directed thereonto so that the air exiting from the air discharge nozzle 38 will sweep over the respective electrode 22.

The four air-conducting tubes 34 are respectively arranged in inserted positions within respective axial bores 42 of protective-cap body 32, the bores 42 being arranged to enter a closed surrounding annular channel 44. The annular channel 44 is supplied with air via an air supply conduit 47 axially arranged externally on immersion-probe body 14. Annular channel 44 is in its radially proximal region, i.e. on its inner side, formed by an outer wall 46 of sensor cartridge 16 and, distally therefrom, by a radially inwardly open annular groove 48 in protective-cap body 32.

In the present exemplary embodiment, protective cap 18 is provided with four elastic locking tabs 50 comprising locking bodies 52 which, in the locking position shown in FIGS. 1-3, grip behind said flange 30 of immersion-probe body 14.

For exchanging the sensor cartridge 16, the locking tabs 50 can be manually bent outwards and the protective cap 18 will be axially withdrawn in the distal direction. Subsequently, after releasing the corresponding fastening means, sensor cartridge 16 can be detached from immersion-probe body 14. Then, a new sensor cartridge 16 can be fastened again to immersion-probe body 14 with the aid of said fastening means. Finally, protective cap 18 will be shifted axially back into place on the sensor cartridge 16 wherein, in the locking position, the four elastic locking tabs 50 will be locked to the flange 30 of immersion-probe body 14, thus holding the protective cap 18 attached to immersion-probe body 14.

Although the present invention has been described and illustrated with reference to specific illustrative embodiments thereof, it is not intended that the present invention be limited to those illustrative embodiments. Those skilled in the art will recognize that variations and modifications can be made without departing from the true scope of the present invention as defined by the claims that follow. It is therefore intended to include within the present invention all such variations and modifications as fall within the scope of the appended claims and equivalents thereof.

What is claimed is:

1. An immersion probe for water analysis, the immersion probe comprising: at least one electrode configured to detect an analyte in water; a probe head with a probe head end side on which the at least one electrode is disposed; and a separate protective cap attached to the probe head so as to be removable in a distal direction, the separate protective cap including a protective cap end side with an electrode opening and an air discharge nozzle, the air discharge nozzle being configured so as to cause air exiting the air discharge nozzle to sweep over the at least one electrode, wherein the separate protective cap includes an annular air channel and an axial air channel, the axial air channel being configured to conduct air from the annular air channel in the air discharge nozzle, and wherein the annular air channel is formed radially proximally by an outer wall of the probe head and radially distally by the separate protective cap.

2. The immersion probe as recited in claim 1, wherein the axial air channel is formed by a separate air-conducting tube.

3. The immersion probe as recited in claim 2, wherein the separate air-conducting tube is made of stainless steel.

4. The immersion probe as recited in claim 1, wherein the probe head is formed by a separate exchangeable sensor cartridge.

5. The immersion probe as recited in claim 1, further comprising an immersion-probe body, wherein the separate protective cap includes at least two locking tabs configured to lock to the immersion-probe body.

6. The immersion probe as recited in claim 1, wherein the at least one electrode includes a membrane on an end side.

7. The immersion probe as recited in claim 1, wherein the separate protective cap is formed by a one-pieced protective-cap body.

8. The immersion probe as recited in claim 1, wherein the separate protective cap comprises rubber-elastic plastic.

* * * * *